US010925873B2

(12) United States Patent
Hall et al.

(10) Patent No.: US 10,925,873 B2
(45) **Date of Patent: *Feb. 23, 2021**

(54) OUTPATIENT MODIFIED RAPID DETOXIFICATION FOR ADDICTION TO ALCOHOL AND DRUGS

(71) Applicants: David Alan Hall, Fort Wayne, IN (US); Terry Lee Yeiter, Warsaw, IN (US)

(72) Inventors: David Alan Hall, Fort Wayne, IN (US); Terry Lee Yeiter, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/185,953

(22) Filed: Nov. 9, 2018

(65) Prior Publication Data

US 2019/0076430 A1 Mar. 14, 2019

Related U.S. Application Data

(63) Continuation-in-part of application No. 15/211,375, filed on Jul. 15, 2016, now Pat. No. 10,166,233.

(60) Provisional application No. 62/192,619, filed on Jul. 15, 2015.

(51) Int. Cl.

| | |
|---|---|
| ***A61K 31/515*** | (2006.01) |
| ***A61K 31/4168*** | (2006.01) |
| ***A61K 31/197*** | (2006.01) |
| ***A61K 31/4045*** | (2006.01) |
| ***G09B 19/00*** | (2006.01) |
| ***A61K 31/215*** | (2006.01) |
| ***A61K 31/451*** | (2006.01) |
| ***A61K 31/46*** | (2006.01) |
| ***A61K 31/496*** | (2006.01) |
| ***A61K 31/5415*** | (2006.01) |
| *A61B 10/00* | (2006.01) |

(52) U.S. Cl.

CPC .......... *A61K 31/515* (2013.01); *A61K 31/197* (2013.01); *A61K 31/215* (2013.01); *A61K 31/4045* (2013.01); *A61K 31/4168* (2013.01); *A61K 31/451* (2013.01); *A61K 31/46* (2013.01); *A61K 31/496* (2013.01); *A61K 31/5415* (2013.01); *G09B 19/00* (2013.01); *A61B 2010/0009* (2013.01)

(58) Field of Classification Search

None

See application file for complete search history.

*Primary Examiner* — Heidi Reese

(74) *Attorney, Agent, or Firm* — Dunlap Bennett & Ludwig, PLLC; Brendan E. Squire

(57) ABSTRACT

A medicament regimen for outpatient modified rapid detoxification for addiction to alcohol and drugs is disclosed. Patients are seen by trained medical professionals who are recovering addicts and alcoholics. The medicament protocol addresses all of the withdrawal symptoms while allowing the patient to safely sleep through the detoxification.

14 Claims, 3 Drawing Sheets

OUTPATIENT MODIFIED RAPID DETOXIFICATION FOR ADDICTION TO ALCOHOL AND DRUGS

CROSS-REFERENCE TO RELATED APPLICATION

This application is a divisional application of U.S. patent application Ser. No. 15/211,375, filed Jul. 15, 2016, and claims the benefit of priority of U.S. provisional application No. 62/192,619, filed Jul. 15, 2015, the contents of which are herein incorporated by reference.

BACKGROUND OF THE INVENTION

The present invention relates to medication assisted detoxification programs and, more particularly, to the detoxification of patients suffering from addiction to alcohol or drugs. Conventional inpatient detoxification programs require 2-5 day patient stays at an inpatient medical or treatment facility, resulting in a much greater expense. Many of these programs do not include follow-up programs. That is, once the patient is released from the treatment facility.

As can be seen, there is a need for an outpatient program that can assist patients with addictions to alcohol or drugs.

SUMMARY OF THE INVENTION

In one aspect of the present invention, a patient detoxification medicament for recovery from a drug addiction on an outpatient basis, includes: a dosage of phenobarbital; a dosage of clonidine; a dosage of baclofen; a dosage of ropinirole; and a dosage of dicyclomine.

The dosage of phenobarbital is about 32.4 mg. The dosage of clonidine is about 0.1 mg. The dosage of baclofen is about 10 mg. The dosage of ropinirole is about 1 mg. The dosage of dicyclomine is about 20 mg.

In other aspects of the invention, the detoxification medicament may also include a dosage of an antidiarrheal or an antinausea medicament selected from the group consisting of promethazine, lomotil, and trazadone. The dosage of promethazine at about 25 mg. The dosage of lomotil at about 2.5 mg. The trazadone at about 100 mg.

In yet other aspects of the invention, the detoxification medicament may also include a dosage of an anti-craving medicament selected from the group consisting of naltrexone, campral, disulfram, vivitrol. The dosage of naltrexone is about 50 mg. The dosage of campral is about 333 mg.

These and other features, aspects and advantages of the present invention will become better understood with reference to the following drawings, description and claims.

DETAILED DESCRIPTION OF THE INVENTION

Figure 1:
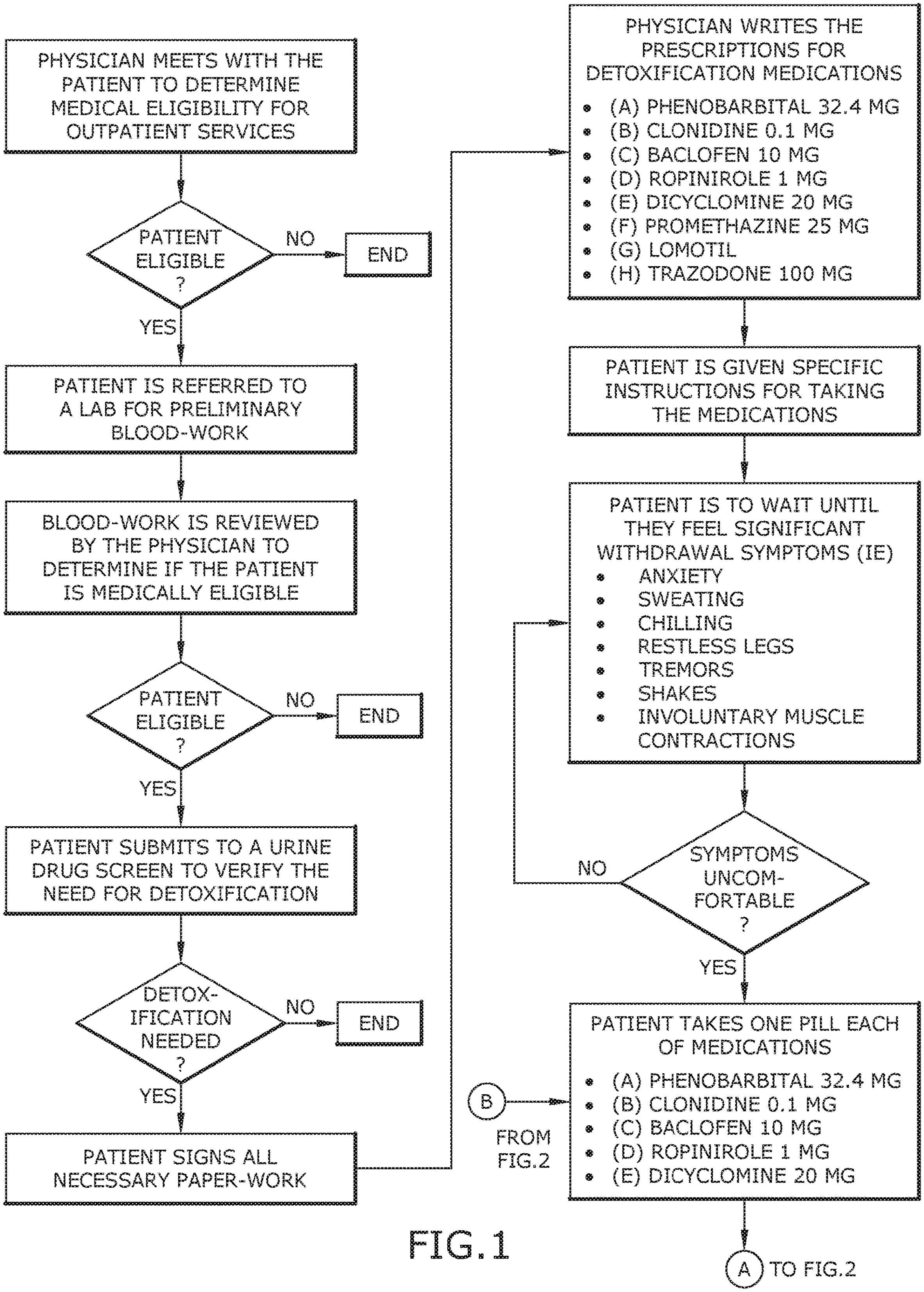
FIG. 1 is a flowchart for a preferred protocol for the detoxification of patients recovering from drug or alcohol addiction in an outpatient setting.
Figure 2:
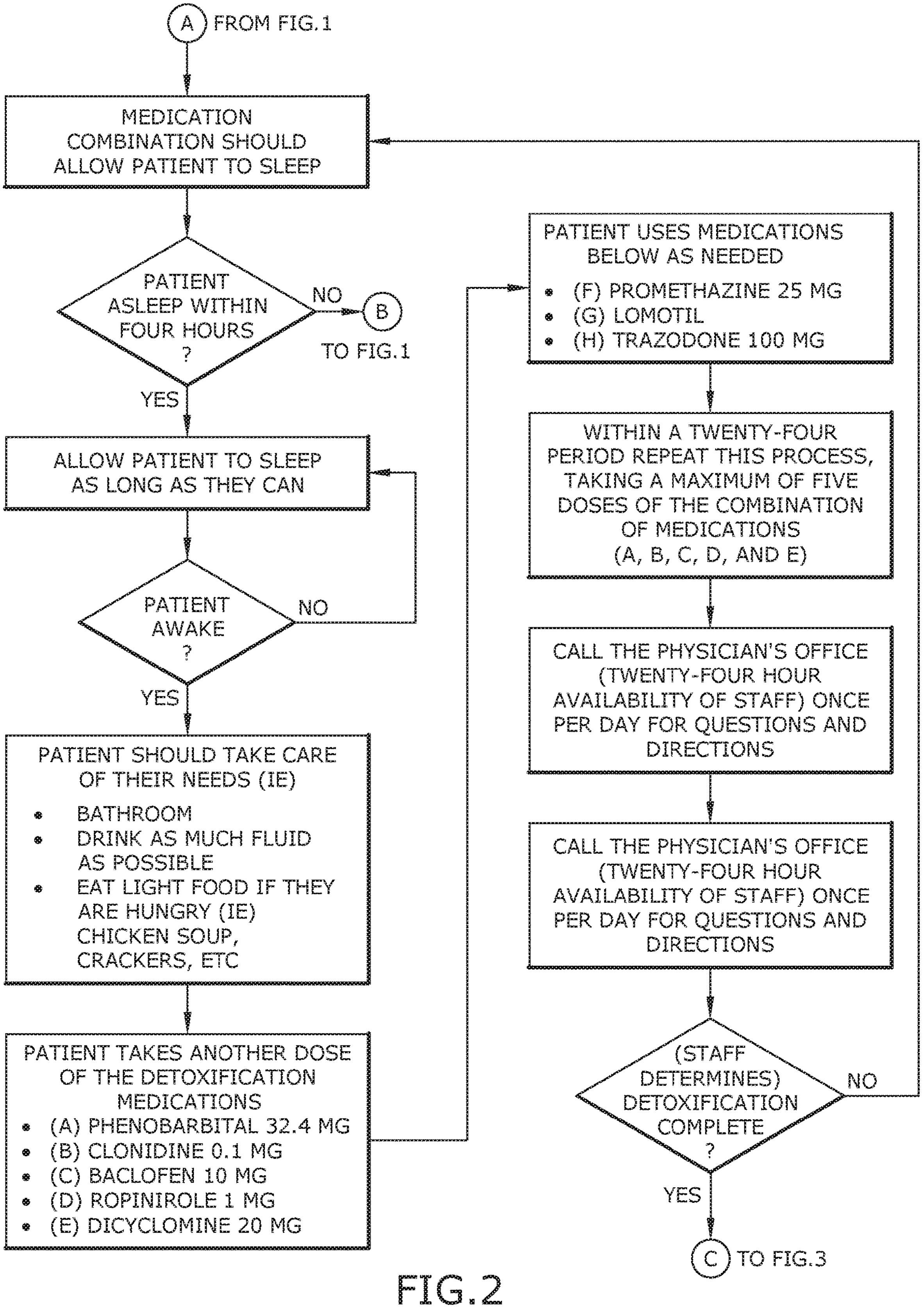
FIG. 2 is a continuation of the flowchart of FIG. 1.
Figure 3:
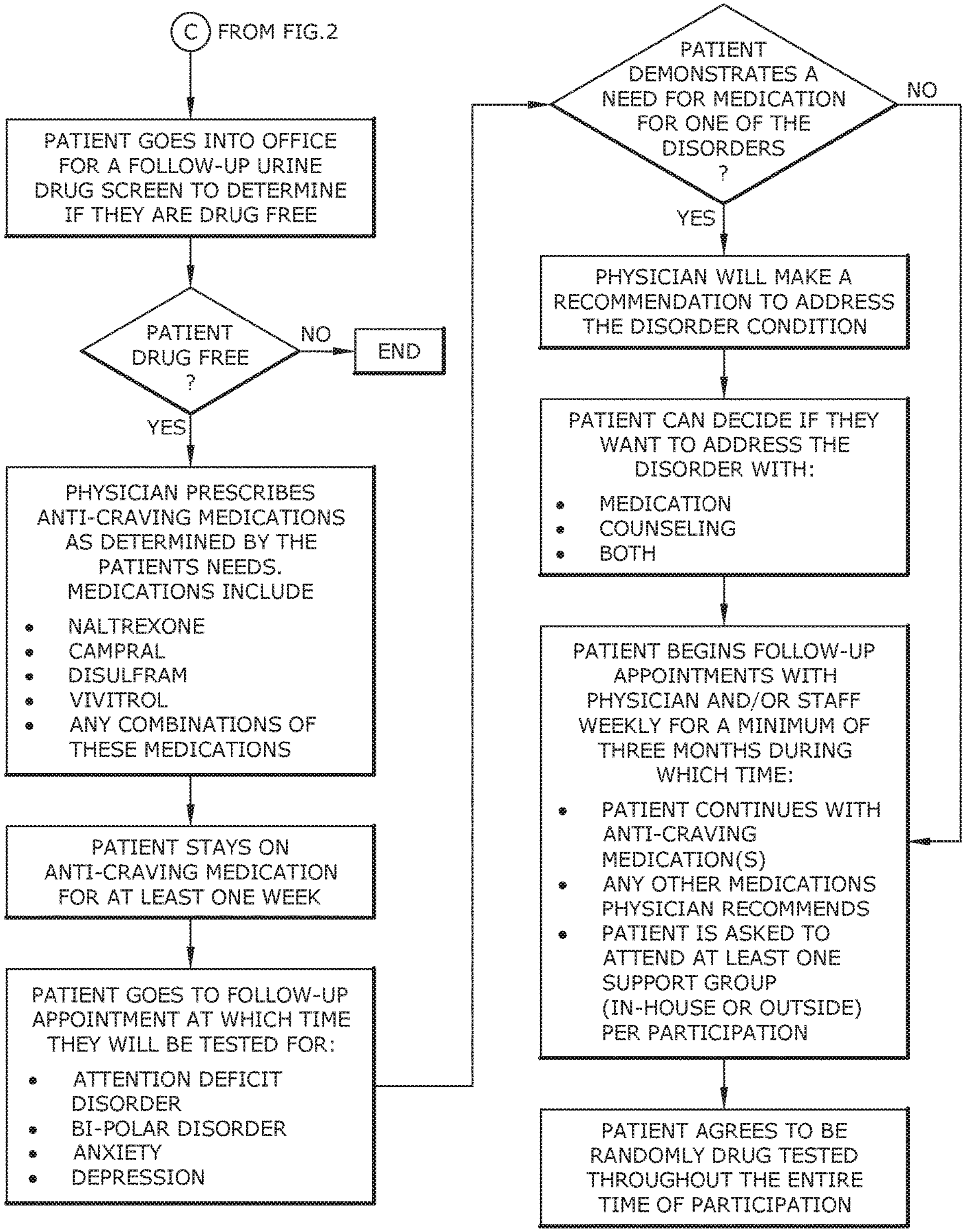
FIG. 3 is a continuation of the flowchart of FIGS. 1 and 2.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a system for outpatient detoxification of patients suffering from addiction to alcohol and drugs. By following the program in an outpatient setting, substantial monetary savings can be realized over programs involving inpatient treatment.

Through the use of a specialized combination of 8 medications, described herein, the patient is able to safely detoxify from alcohol and drug addiction on an outpatient basis at the direction of a medical doctor. The initial detoxification is followed up by 3 months of weekly visits to the doctor for prescriptions for anticravings medications, such as Naltrexone (50 mg), Campral (333 mg). Concurrently, during this 3 month period, the patient is provided weekly counseling sessions.

The claimed invention differs from what currently exists. Following the regimen disclosed herein, the patient is able to undergo detoxification treatment in the comfort of their own home. The patient is provided telephonic access to the doctor and trained medical staff 24 hours a day, 7 days per week, and with greatly reduced cost.

Some hospital staffs are often poorly trained in detoxification methods and are not aware of the psychological needs of addicted patients. Quite often access to inpatient detoxification is curtailed by insurance or other cost considerations. An aspect of our invention is that, the recovering patients are seen by trained professionals, who are often themselves recovering drug addicts and alcoholics. The medication protocol addresses all of the withdrawal symptoms, while allowing the patient to safely sleep through the detoxification process.

The following protocol is presented for the outpatient detoxification program according to our invention:

1. Patient meets with a doctor to determine the patient is medically eligible for participation in the outpatient program. Eligibility requirements include: a desire to quit using alcohol and/or drugs of abuse, blood work within normal ranges, no allergies to any of the medications used for detoxification or cravings.

2. Doctor prescribes the following detoxification medications including:

A) Phenobarbital (32.4 mg);
B) clonidine (0.1 mg);
C) baclofen (10 mg);
D) ropinirole (1 mg);
E) dicyclomine (20 mg);
F) promethazine (25 mg);
G) lomotil (2.5 mg); and
H) trazodone (100 mg).

3. The Patient is given specific instructions for order and amount of medications to be taken, according to the following:

a. The patient should wait until they feel significant withdrawal symptoms, i.e. anxiety, sweating and chilling, restless legs, tremors, shakes and involuntary muscle contractions.

b. Once the withdrawal symptoms become uncomfortable the patient takes one pill from each of the prescribed medications A., B., C., D., and E. This combination of medications should allow the patient to sleep comfortably.

c. If the patient is unable to sleep within 4 hours of the previous dosage administration, the patient is to take another combination of the five (5) drugs A., B., C., D., and E.

d. Once the patient is asleep, they should be allowed to sleep as long as they can.

e. When the patient awakes, they should use the bathroom, if necessary, and should drink as much fluids as possible. Should the patient get hungry, they should eat light food, such as chicken soup, crackers, and the like.

f. The patient should then take another dose of the detoxification medications A., B., C., D., and E. If necessary, the patient should take medications F., G., and H, as needed and prescribed.

g. Repeat this process for a twenty-four (24) hour period, taking a maximum of five (5) doses of the combination A., B., C., D., and E within a twenty-four hour period.

h. The patient should call the physician's office (24 hour availability of staff) once per day for questions and further directions.

Repeat steps 3. a. through 3. h., calling the office daily until staff evaluation determines that the detoxification is complete.

4. When detoxification is complete as verified by a subsequent urine drug screen testing for the drug/alcohol that the patient is being treated for to make sure that the patient is testing negative. Then a prescription is given by the doctor for anti-craving medications, such as: Naltrexone (50 mg) and Campral (333 mg).

5. After the patient has been on the anti-craving medication(s) for at least one (1) week, they are given a follow-up appointment, at which time they will be tested for Attention Deficit Disorder, Bi-Polar Disorder, anxiety and depression. If the patient demonstrates a need for medication for any of those disorders, then the physician will make a recommendation and the patient can decide if they desire to address the disorder condition with medication, or counseling, or a combination thereof.

6. The patient then begins weekly follow-up appointments with the physician and/or staff for a minimum of three (3) months during which time they continue with the anti-craving medication(s) and any other medication that the physician recommends. Additionally, the patient attends at least one (1) support group (in-house or outside) meeting per week, in addition to individual therapy sessions with a counselor or physician as needed.

7. For participation in the program, the patient agrees to submit to random urine drug screens, to monitor compliance throughout the duration of the program. If the patient tests positive for alcohol and/or drug use, their case is reviewed by staff to determine if they can continue on the program or need to be referred to an inpatient treatment program.

It is important that the procedure be followed in numerical order for the patient to have the most comfortable detoxification, and for the best possible outcome. Taking any shortcut can result in a failed attempt to detoxify. For a doctor and staff to use this procedure they would need to know the symptoms of withdrawal to understand that the specific order of medications used in the withdrawal process is extremely important for a successful detoxification.

Typical symptoms of withdrawal includes anxiety, sweating, chilling tremors, involuntary muscle contractions, restless legs, abdominal pain and cramping, nausea, vomiting, diarrhea, and insomnia. Medications used for these symptoms in order of use for the particular symptom; A) Phenobarbital (32.4 mg), B) Clonidine (0.1 mg), C) Baclofen (10 mg), D) Ropinirole (1 mg), #) Docyclomine (20 mg), F) Promethazine (25 mg), G) Lomotil (2.5 mg), H) Trazodone (100 mg). The order of use of the medications A, B, C, D, E, to begin the detoxification should not be varied. Medications F, G, and H, are to be used for symptoms such as diarrhea, nausea, and vomiting.

If the patient is determined to be appropriate medically for outpatient detoxification then the medication regimen according to the present invention, if followed as directed, will be successful in achieving a safe, comfortable, affordable outcome for the patient.

A doctor would need to know the specific drugs, the strengths of the drugs, and the order that they are used in to be successful. The components cannot be interchanged in any way or the procedure will not work. This is a medical procedure that should only be used in the foregoing manner to solve the problem of outpatient detoxification.

It should be understood, of course, that the foregoing relates to exemplary embodiments of the invention and that modifications may be made without departing from the spirit and scope of the invention as set forth in the following claims.

What is claimed is:

1. A detoxification medicament comprising:
a dosage of phenobarbital;
a dosage of clonidine;
a dosage of baclofen;
a dosage of ropinirole; and
a dosage of dicyclomine.

2. The detoxification medicament of claim 1, wherein the dosage of phenobarbital is about 32.4 mg.

3. The detoxification medicament of claim 1, wherein the dosage of clonidine is about 0.1 mg.

4. The detoxification medicament of claim 1, wherein the dosage of baclofen is about 10 mg.

5. The detoxification medicament of claim 1, wherein the dosage of ropinirole is about 1 mg.

6. The detoxification medicament of claim 1, wherein the dosage of dicyclomine is about 20 mg.

7. The detoxification medicament of claim 1, wherein:
the dosage of phenobarbital is about 32.4 mg;
the dosage of clonidine is about 0.1 mg;
the dosage of baclofen about 10 mg;
the dosage of ropinirole about 1 mg; and
the dosage of dicyclomine is about 20 mg.

8. The detoxification medicament of claim 1, further comprising:
a dosage of an antidiarrheal or an antinausea medicament selected from the group consisting of promethazine, lomotil, and trazadone.

9. The detoxification medicament of claim 8, wherein the dosage of the antidiarrheal or the antinausea medicament comprises:
promethazine at about 25 mg.

10. The detoxification medicament of claim 8, wherein the dosage of the antidiarrheal or the antinausea medicament comprises:
lomotil at about 2.5 mg.

11. The detoxification medicament of claim 8, wherein the dosage of the antidiarrheal or the antinausea medicament comprises:
trazadone at about 100 mg.

12. The detoxification medicament of claim 8, further comprising:
a dosage of an anti-craving medicament selected from the group consisting of naltrexone, campral, disulfram, vivitrol.

13. The detoxification medicament of claim 12, wherein the dosage of naltrexone is about 50 mg.

14. The detoxification medicament of claim 12, wherein the dosage of campral is about 333 mg.

* * * * *